United States Patent

Migita

Patent Number: 5,668,845
Date of Patent: Sep. 16, 1997

[54] COMPUTED-TOMOGRAPHY APPARATUS AND CONTROL METHOD THEREOF

[75] Inventor: Shinichi Migita, Ryugasaki, Japan

[73] Assignee: Hitachi Medical Corp., Tokyo, Japan

[21] Appl. No.: 611,851

[22] Filed: Mar. 6, 1996

[30] Foreign Application Priority Data

Apr. 13, 1995 [JP] Japan .................... 7-088258

[51] Int. Cl.⁶ .................................... G21K 5/10
[52] U.S. Cl. .................................... 378/4; 378/146
[58] Field of Search .................... 378/4, 146, 205, 378/15, 20

[56] References Cited

U.S. PATENT DOCUMENTS

| | | | |
|---|---|---|---|
| 4,580,219 | 4/1986 | Pelc et al. | 378/901 |
| 5,212,717 | 5/1993 | Hada | 378/4 |
| 5,224,135 | 6/1993 | Toki | 378/4 |
| 5,228,070 | 7/1993 | Mattson | 378/108 |
| 5,386,452 | 1/1995 | Toki | 378/4 |

*Primary Examiner*—Don Wong
*Attorney, Agent, or Firm*—Antonelli, Terry, Stout & Kraus, LLP

[57] ABSTRACT

A computed-tomography apparatus acquires a cross-sectional image of an object from projection data obtained by scanning the object with radiation while rotating a scanner around the object. One of rotation positions of the scanner having a smaller attenuation of radiation is determined. The operation of the scanner is controlled to start the scan from the rotation position having the smaller attenuation. Individual weights are assigned to projection data in a predetermined rotation angle range near a scan start rotation position of the scanner and near a scan end rotation position thereof and projection data in a rotation angle range opposite to the predetermined rotation angle range, respectively. The weighted projection data and unweighted projection data are used for determining corrected data for the entire circumference of the object to generate a cross-sectional image based thereon. The range of a correction region can be changed in accordance with a scan start position so that when the scan start position is not suited in a direction having a smaller attenuation, the correction region is narrowed to optimize the effect of suppression of background noises and artifacts. A plurality of scan start positions can be set on the locus of scan rotation of the scanner so that the actual scan is started from the scan start position which is first detected after the point of time when a scan start signal is given.

25 Claims, 7 Drawing Sheets

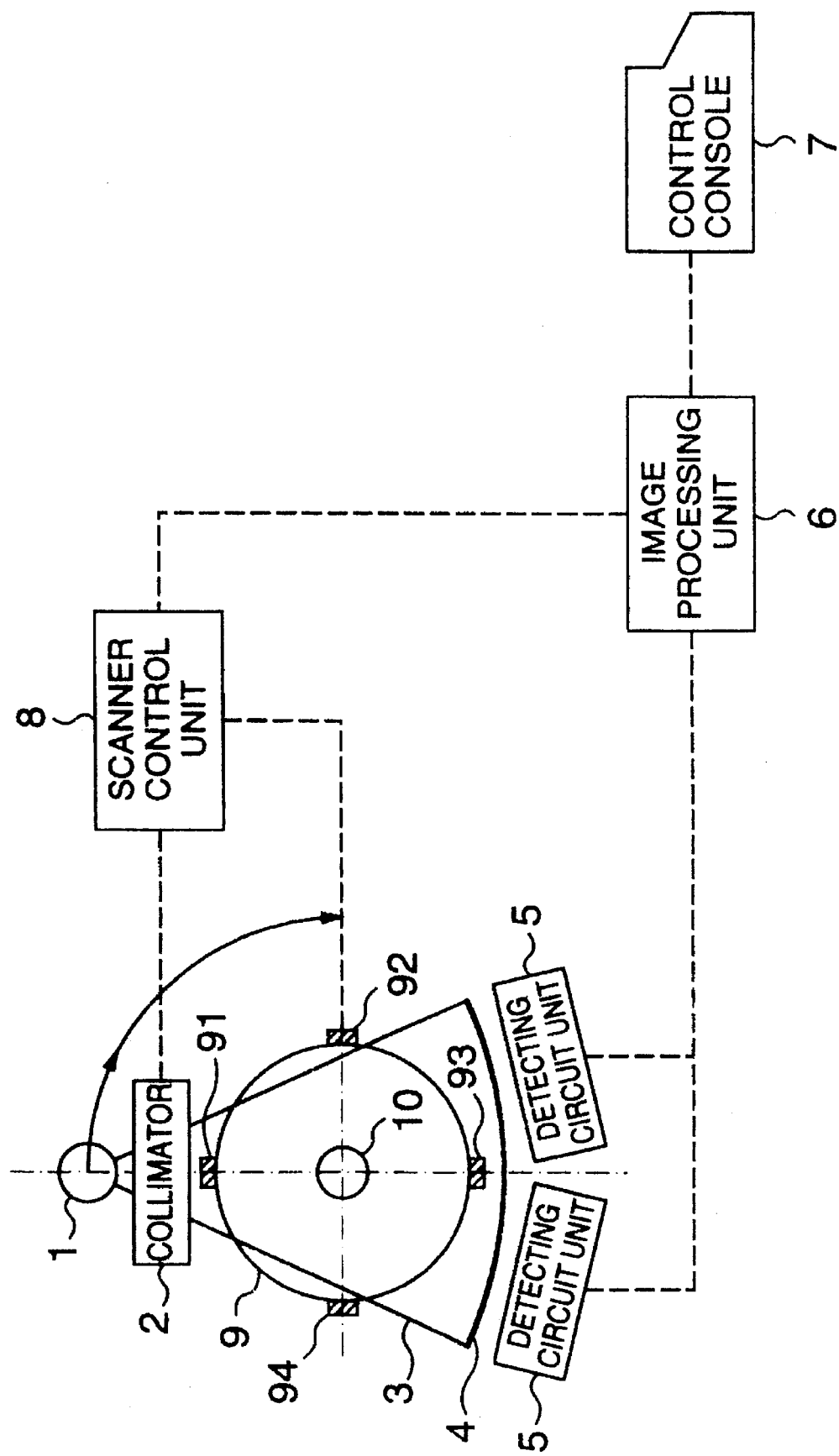

COMPUTED-TOMOGRAPHY APPARATUS AND CONTROL METHOD THEREOF

BACKGROUND OF THE INVENTION

The present invention relates to a computed-tomography (CT) apparatus for acquiring a cross-sectional image of an object by use of X-rays, ultrasonic waves or the like, and more particularly to such a CT apparatus suitable for use as a medical diagnosis apparatus.

In recent years, CT apparatuses for acquiring cross-sectional images of objects have widely been used especially as medical diagnosis apparatuses for diagnosing patients. Such apparatuses include an X-ray CT apparatus which uses X-rays, a radiography isotope (RI) CT, ultrasonic CT and image intensifier (I.I) CT apparatuses in which the measurement of projection data is made from the circumferential directions of an object around the object to reconstruct an image, and so forth.

In a general X-ray or other type CT apparatus, a time for measuring an object at a predetermined slice position through the scan of the entire circumference of the object (or so-called 360° one-slice measurement time) differs according to a plurality of measurement modes which can be changed. Usually, this measurement time is 1 to 9 seconds. Therefore, it is general that an operator of the apparatus selectively uses the optimum measurement mode in accordance with the size of an object, a part to be subjected to diagnosis or the purpose of diagnosis.

If a motion such as the motion of an object or the motion of internal organs of the object occurs during the above-mentioned measurement time, artifacts called motion artifacts are generated due to this motion. Owing to the artifacts, an accurate diagnosis from the acquired cross-sectional image becomes difficult. The well known method for solving such a technical problem is a measurement data correcting method disclosed by, for example, U.S. Pat. No. 4,580,219 issued on Apr. 1, 1986 and entitled "METHOD FOR REDUCING IMAGE ARTIFACTS DUE TO PROJECTION MEASUREMENT INCONSISTENCIES". This correction method is generally called bowel gas correction.

The bowel gas correction method will now be explained briefly by use of FIG. 6. In a usual CT apparatus, a measurement start position of a scanner is fixed beforehand at a predetermined position. The scanner starts the measurement from the predetermined measurement start position and makes a 360° scan over the entire circumference of an object to obtain projection data of the object. A measurement end position assumes the same position as the measurement start position. Therefore, the first image and the last image will be consistent with each other if there is no motion of the object during an interval between the measurement start and end positions. In the actual measurement, however, when the object moves during the measurement interval, discontinuities are generated between measurement data at the measurement start and end positions. Owing to the discontinuities of measurement data, inconsistencies called misregistration differences appear between the projection data measurement start and end positions. The inconsistencies cause the generation of motion artifacts after image reconstruction. For such circumstances, data correction called bowel gas correction is made in order that the continuity of data in a predetermined rotation angle range (hereinafter referred to as correction region A) near each of the measurement start and end positions is improved even if any motion of the object is involved.

In general, the same result is given by CT projection data obtained by measuring an object from directions which are different by 180°. In the bowel gas correction, the contribution of projection data to the reconstruction of a cross-sectional image is modified. More particularly, the contributions of projection data near the measurement (or scan) start position and projection data near the measurement end position providing the cause of artifacts are reduced while the contributions of projection data near a position opposite to the measurement start position with 180° therebetween and projection data near a position opposite to the measurement end position with 180° therebetween are increased. Namely, the cross-sectional image of one slice is generated by assigning a weight smaller than 1 to projection data in the predetermined rotation angle range (or the correction region A in FIG. 6) and assigning a weight greater than 1 to projection data in a rotation angle range (hereinafter referred to as correction region B) opposite to the correction region A. The correction regions A and B are positioned opposite to each other and have the same rotation angle range.

The weight takes the smallest value (zero) at the measurement start position and the measurement end position and is gradually increased with the increase of a distance from the measurement start position and the measurement end position. Also, the weight takes the greatest value at the middle portion of the correction region B opposite to the measurement start position and the measurement end position and is gradually decreased with the increase of a distance from the correction region B. The case where no bowel gas correction is made corresponds to the case where the same weight (1.0) is used at any position, as shown by dotted line in FIG. 6.

In a medical diagnosis CT apparatus such as X-ray CT apparatus, a measurement method is generally performed in which a contrast agent is injected into a blood vessel to emphasize constrastive differences between various tumors and normal tissues, thereby facilitating the diagnosis of a patient. In this method, the contrast agent flows away as the blood circulates. Therefore, the timing of injection of the contrasting agent and the timing of start of measurement provide important factors for accurate diagnosis. Particularly, in the tomographic imaging of a patient with an impediment in consciousness or an infant, an operator starts the measurement at a timing when the object has no motion. In such cases, the concurrency of a measurement start instruction (or operation) by the operator and the start of measurement by the diagnosis apparatus is an important task for the purpose of providing a cross-sectional image which has a high diagnostic value.

Under such backgrounds, a continuously rotatable scanner having, for example, a slip ring mounted thereon has recently been used widely. In such a scanner, the measurement start position can be set freely. Therefore, it is possible to improve the concurrency of an operator's desired measurement start timing and the start of measurement by the diagnosis apparatus, thereby shortening a time for a series of measurements.

SUMMARY OF THE INVENTION

FIGS. 7A, 7B, 7C and 7D show the examples of cross-sectional images of a human belly subjected to bowel gas correction. As shown, linear artifacts 20 appear in the image. A plurality of short lines designated by reference numeral 21 are background noises. In the cases of FIGS. 7A and 7B, the correction region A (see FIG. 6) for bowel gas correction is set to be wide as compared with that in the cases of FIGS. 7C and 7D. As the correction region A becomes wider, the continuity between data near the measurement start position and data near the measurement end position is improved. Accordingly, the artifacts 20 in the image of FIG. 7A are reduced as compared with those in the image of FIG. 7C and therefore give a reduced influence on the diagnosis of the image of internal organs. On the contrary, in the case of FIG. 7C in which the correction region A is narrow, the artifacts 20 appear strongly in the image.

However, in the case where the correction region A is set to be wide, the background noises 21 appear strongly in the image, as apparent from FIG. 7B. On the contrary, in the case where the correction region A is set to be narrow, the background noises 21 are weakened, as apparent from FIG. 7D. The reason why the background noises are increased when the correction region for bowel gas correction is wide, is that the range of data giving no contribution to image generation is increased due to the correction, thereby deteriorating the efficiency of utilization of X-rays with the relative increase of the background noises. Consequently, the bowel gas correction involves a problem that the suppression of artifacts is accompanied by the increase of background noises.

In the conventional CT apparatus, a cross-sectional image obtained through measurement from an axial direction having a large attenuation of radiation is characterized in that conspicuous background noises appear along that axial direction. FIG. 8 shows projection data 24 which is obtained by irradiating an elliptic object 22 with X-rays emitted from an X-ray source suited at a position 23 on the x axis and projection data 26 which is obtained by irradiating the object 22 with X-rays emitted from an X-ray source suited at a position 25 on the y axis. As apparent from FIG. 8, the thickness of the object 22 is large in the x-axis direction and hence the attenuation of X-rays in the x-axis direction is larger than that in the y-axis direction. In this case, background noises will be conspicuous in the image data obtained through the measurement from the x-axis direction.

If a direction having a large attenuation (such as the x-axis direction in the above example) coincides with a measurement start position by chance, the bowel gas correction will cause a further increase of background noises. In an image having a low contrast, the background noises make the diagnosis difficult. In addition, artifacts are an obstacle to the diagnosis.

In medical diagnosis apparatuses for making the diagnosis of patients for the purpose of medical diagnosis, a variety of combinations may be employed in accordance with the shapes of objects such as patients and the measurement conditions. Therefore, it is desired to acquire a high-quality cross-sectional image by setting the optimum bowel gas correction region for all the combinations while synthetically considering merits and demerits based on the shapes of objects and the measurement conditions. In the practical state of the conventional CT apparatus, however, it is difficult to satisfy such a requirement.

The present invention has been completed on the basis of the present inventors knowledge of the bowel gas correction in the prior art and the relationship between background noises and an object as mentioned above. ACT apparatus according to the present invention provides an image in which the increase of background noises necessarily associated with the bowel gas correction is reduced to the possible minimum while the motion artifact correction effect based on the bowel gas correction is maintained to the optimum and the shape of an object and the difference in attenuation depending on the axial direction of the object are taken into consideration. One object of the present invention is to provide a CT apparatus which can provide a high-quality cross-sectional image necessary for accurate diagnosis of a patient in the capacity of a medical diagnosis apparatus.

ACT apparatus according to the present invention realizes the concurrency of the operation of measurement start by an operator and the actual measurement start. In the above-mentioned continuously rotatable scanner having a slip ring mounted thereon, the operation of measurement start by the operator substantially coincides with the actual measurement start. However, in a scanner based on a control method in which the operation of measurement start is performed from a certain fixed position, there may occur a situation in which a measurement instruction is issued by an operator when the scanner has already passed the measurement start position. In this case, there is generated a time delay until the scanner reaches the measurement start position again. In a measurement mode in which a long measurement (or scan) time is set for one slice, not only such a time delay but also the variations of a time from the timing of measurement instruction issuance until the actual measurement start are dominant problems in making the quantitative analysis of an image. Therefore, another object of the present invention is to provide a CT apparatus which can provide a high-quality cross-sectional image by minimizing a time delay from the designation of measurement start by an operator until the actual measurement start irrespective of the lengths of scan times determined by measurement modes which may be employed in a scanner based on a control method with the operation of measurement start performed from a fixed position.

In a CT apparatus according to an embodiment of the present invention, the scan is started from a direction having a small attenuation of radiation to acquire a cross-sectional image of an object in which background noises and motion artifacts are suppressed to the possible minimum. In the CT apparatus of this embodiment, one of rotation positions of a scanner having a smaller attenuation of radiation is determined. The operation of the scanner is controlled so that the scan is started from the determined rotation position having the smaller attenuation. Individual weights are assigned to projection data in a predetermined rotation angle range including the vicinity of a scan start rotation position of the scanner and the vicinity of a scan end rotation position thereof and projection data in a rotation angle range opposite to the predetermined rotation angle range, respectively. The projection data assigned with the weights and projection data assigned with no weight are used to determine corrected data for the entire circumference of the object, thereby generating a cross-sectional image of the object on the basis of the corrected data.

In a CT apparatus according to another embodiment of the present invention, the range of a correction region is changed in accordance with a scan start position. If the scan start position is not suited in a small attenuation of radiation, the correction region is narrowed to optimize the effect of suppression of background noises and artifacts. In the CT apparatus of this embodiment, one of rotation positions of a scanner having a smaller attenuation of radiation is determined. Further, a scan start rotation position of the scanner is detected. In the case where the detected scan start rotation position is not suited in the rotation position having the smaller attenuation, a predetermined rotation angle range including the vicinity of a scan start rotation position of the scanner and the vicinity of a scan end rotation position thereof is narrowed. Individual weights are assigned to projection data in the predetermined rotation angle range and projection data in a rotation angle range opposite to the predetermined rotation angle range, respectively. The projection data assigned with the weights and projection data assigned with no weight are used to determine corrected data for the entire circumference of an object, thereby generating a cross-sectional image of the object on the basis of the corrected data.

In a CT apparatus according to a further embodiment of the present invention, a delay corresponding to a time from the operation of scan (or measurement) start by an operator until the actual scan start and the variations of such a time are minimized by setting a plurality of scan start positions on the locus of scan rotation of the scanner. In the CT apparatus of this embodiment, a plurality of scan start positions are detected during the rotation of the scanner. The actual scan is started from a scan start position which is first detected from the point of time when a scan start signal is issued.

BRIEF DESCRIPTION OF THE DRAWINGS

FIG. 1 is a block diagram showing the schematic construction of an X-ray medical diagnosis CT apparatus according to an embodiment of the present invention;

DESCRIPTION OF THE PREFERRED EMBODIMENTS

Figure 2A:
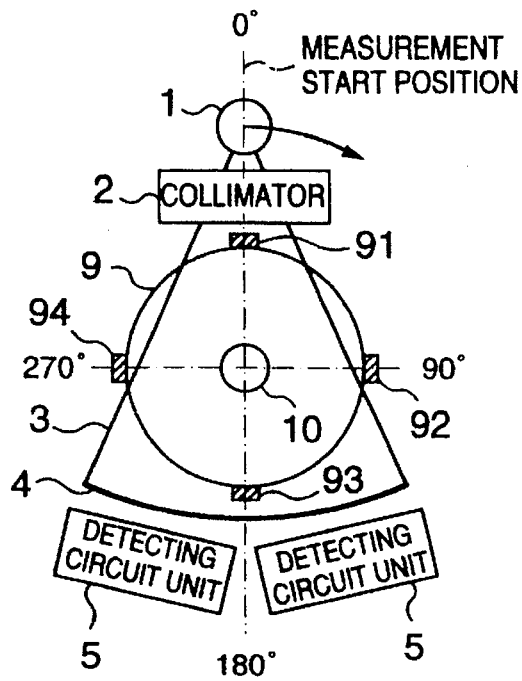
FIGS. 2A, 2B, 2C and 2D are views for explaining a relationship between a measurement start position of a scanner and a position sensor in the X-ray medical diagnosis CT apparatus according to the embodiment of the present invention.

The details of embodiments of the present invention will now be explained in reference to the accompanying drawings.

FIG. 1 shows the schematic construction of an X-ray medical diagnosis CT apparatus according to an embodiment of the present invention. This CT apparatus is a so-called "third generation" type CT apparatus in which the measurement can be made with a measurement start position made variable. Also, this CT apparatus is a so-called X-ray CT apparatus which uses X-rays.

In the X-ray CT apparatus shown in FIG. 1, an operator inputs various instructions and measurement conditions necessary for measurement by use of a control console 7 prior to the measurement. An image processing unit 6 reads the contents of inputted instructions and measurement conditions to sent desired control signals to components, such as a high voltage generator for X-rays, a bed unit (both not shown) and a scanner control unit 8, which form the CT apparatus. After the communication of the control signals between those components, the image processing unit 6 takes a measurement start instruction waiting condition at the point of time when the preparations for measurement are completed. In this waiting condition, the measurement is started in a preliminarily inputted measurement mode by an operator's measurement start instruction.

Next, explanation will be made of the structure of a scanner. As apparent from FIG. 1, the internal structure of the scanner is such that a detector 4 is provided at a position opposite to an X-ray tube 1 and X-rays emitted from the X-ray tube 1 are narrowed in a slice direction (or scanner depth direction) by a collimator 2 to form an X-ray beam 3. In the detector 4, X-rays transmitted through an object such as a patient are converted into an electric signal. The electric signal is amplified by a detecting circuit unit 5. The amplified signal is converted from an analog signal into a digital signal which is in turn sent as projection data to the image processing unit 6. In the image processing unit 6, the projection data is subjected to a predetermined operation processing by an operating unit (not shown) to make image reconstruction. The reconstructed cross-sectional image is displayed on a display device of the control console 7.

In a general type of scanner, restrictions are imposed on the rotation angle of the scanner since it is difficult to freely move a high voltage cable for supplying a high voltage to an X-ray tube. However, the scanner in the embodiment of the present invention has a structure in which its measurement start position can be changed. More particularly, the scanner of the present embodiment is constructed such that it can make a rotation equal to or more than 1.25 revolutions to ensure a measurement angle which is 360°+90° at the minimum. The angle 360° corresponds to the range of measurement or scan and the angle 90° corresponds to a rotation region for acceleration and deceleration. In the case where a scanner using a slip ring mechanism is used as another scanner to which the present invention can be applied, the slip ring transmits/supplies various control signals therethrough. The slip ring also transmits supply powers for the collimator 2, the detector 4 and the detecting circuit unit 5 and a high voltage power for the X-ray tube 1 from a scanner base to a scanner rotating base. Further, a measurement signal of the detector 4 is transmitted through the slip ring from the scanner rotating base to the scanner base. Such a construction enables a measurement by the continuous rotation of the scanner. In the general type of scanner, measurement start points are provided at two positions adjacent to each other by 90°, in order to achieve the start of measurement from at least the direction of axis of ordinate (or vertical direction) and the direction of axis of abscissa (or horizontal direction). Namely, any one of a set of positions 91 and 92, a set of positions 92 and 93, a set of positions 93 and 94 and a set of positions 94 and 91 shown in FIG. 1 are the two measurement start points which are adjacent to each other by 90°. On other hand, in the slip ring scanner, no restriction is imposed on the rotation angle and therefore a plurality of measurement start points can be set arbitrarily. In the present embodiment, four measurement start points are provided at the 90° intervals of the vertical axis and the horizontal axis.

Next, brief explanation will be made in conjunction with the case where a plurality of measurement start points are judged while the measurement from any measurement start angle is variably controlled.

In the embodiment shown in FIG. 1, a disk-like position information plate 9 is fixed on the scanner rotating base. A measurement start point is marked (with the form of a hole or a signal) at one point on the circumference of the position information plate 9. The position information plate 9 rotates as the scanner rotates. Position sensors 91 to 94 for reading the mark of the measurement start point (or measurement start mark) are fixed on the scanner base side which is not rotated. When the measurement start mark on the position information plate 9 passes one of the position sensors 91 to 94, a detection signal from the position sensor is delivered to the scanner control unit 8 which makes the whole control of a measurement operation of the scanner. The scanner control unit 8 determines the position of one of the sensors 91 to 94 which delivers the detection signal. Thus, the scanner control unit 8 can control the timing of a measurement start position while confirming the rotation angle of the scanner. In the case where the position information plate 9 is marked beforehand with encoded signals at positions corresponding to the four angle positions, the judgement of scanner angle information is possible by reading a position information signal from only a position sensor (for example, 91) fixed at one location. Also, there may be realized various control methods including a method in which a rotating encoder sensor is directly attached on the scanner rotating base side so that angle information is judged directly from an encoder signal of the rotating encoder sensor to control a measurement start position.

The image processing unit 6 and the scanner control unit 8 can be realized by a general computer having a control program incorporated therein.

Figure 2B:
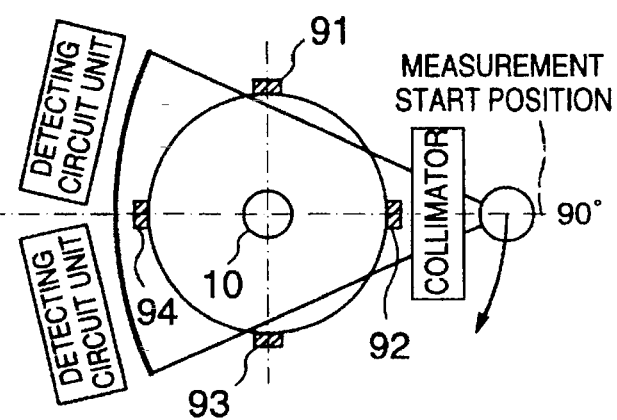
Figure 2C:
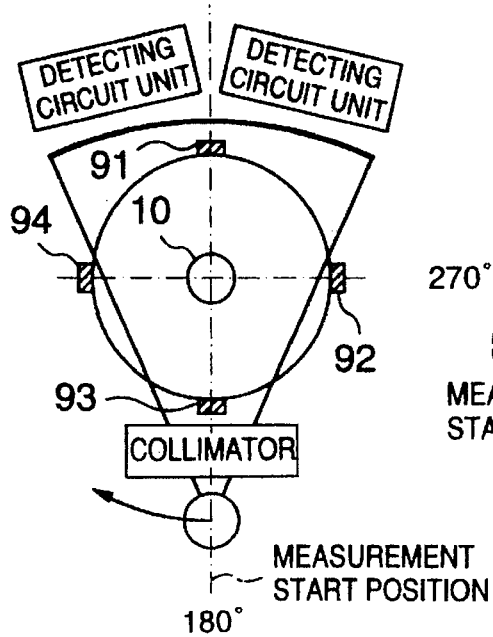
Figure 2D:
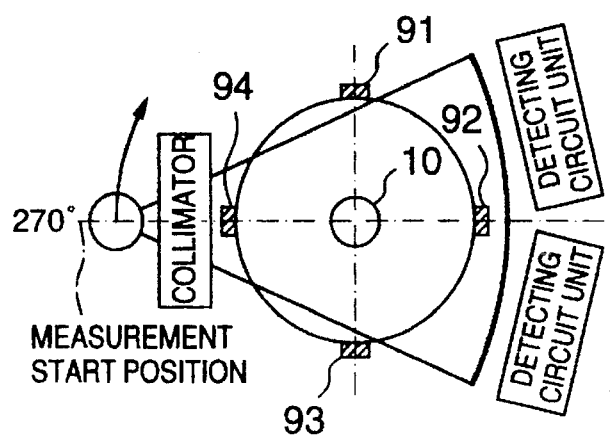

FIGS. 2A, 2B, 2C and 2D are views showing the conditions of the scanner at the time of measurement start at the four rotation angles attained by the above-mentioned mechanism which is capable of making the variable control of a measurement start position. FIG. 2A shows the condition of measurement start from a 0° position at which the X-ray tube 1 is positioned just above the object 10. FIG. 2B shows the condition of measurement start from a 90° position at which the X-ray tube 1 is positioned on the right side of the object 10. FIG. 2C shows the condition of measurement start from a 180° position at which the X-ray tube 1 is positioned just under the object 10. FIG. 2D shows the condition of measurement start from a 270° position at which the X-ray tube 1 is positioned on the left side of the object 10. The measurement is made with the four measurement start positions (two positions in the general type of CT scanner) freely interchanged.

The flow of the operation in the above-mentioned CT apparatus and the details of a method for correction of obtained measurement data will now be explained by use of FIGS. 3 to 5.

Figure 3:
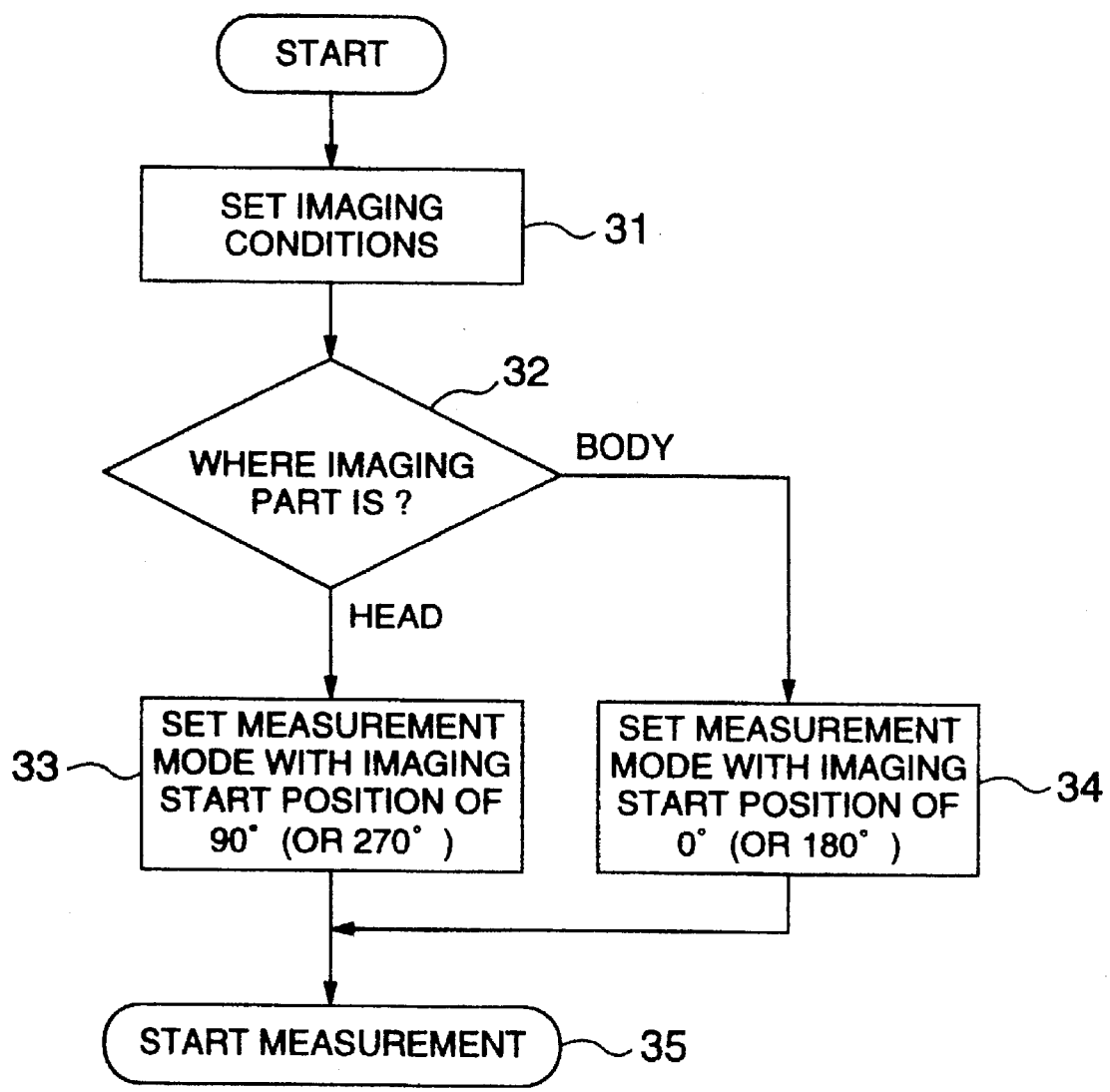
FIG. 3 is a flow chart for explaining an imaging operation in an embodiment of an X-ray medical diagnosis CT apparatus according to the present invention.

FIG. 3 shows a flow for realizing a measurement method in which the measurement is made in such a manner that a difference in attenuation between the vertical and horizontal axis directions of an object to be measured is judged to perform the measurement with a measurement start position set to an axis direction having a small attenuation in the object.

In this measurement method, an operator inputs various settings and measurement conditions necessary for measurement by the control console unit 7 (step 31). In this case, the orientation and size of an object 10 to be measured, imaging conditions for respective parts to be measured, and so forth are protocol-inputted or inputted in one collective set. Examples of the orientation of the object include a supine position (in which the object lies face up or lies on its back), a prone position (in which the object lies face downward or lies on its belly) and a sideway position (in which the object faces sideways, turns sideways or lies on its side). The orientation of the object is inputted since there is a need to display the orientation of a cross-sectional image to be ultimately displayed.

In step 32, a relationship in the quantity of attenuation in the object 10 is judged. In general, the cross section of a human body as an object in a medical diagnosis CT apparatus is circular or elliptic. Therefore, if a part to be imaged is a head, the vertical axis direction assumes the major axis direction of the ellipse in state in which the head lies face up. If the part to be imaged is a body, the horizontal axis direction assumes the major axis direction of the ellipse in a state in which the body lies on its back. In the case where the object has an elliptic cross section, the attenuation is large in the major axis direction of the ellipse. In the present embodiment, therefore, an imaging start position is determined in accordance with an imaging part to be measured. More particularly, the object information and measurement conditions inputted beforehand by the operator are read by the image processing unit 6. Thereby, the image processing unit 6 can determine, through the above-mentioned procedure of judgement, which one of the vertical and horizontal axis directions of each object has a smaller attenuation.

The image processing unit 8 has a memory (not shown) in which information indicating a relationship in the quantity of attenuation for the kind and direction of each object is stored. The judgement of attenuation is made by referring to the information in the memory in accordance with the inputted protocol information. For example, in the case where the object is the head of a human and lies face up, the 90° direction or 270° direction (FIG. 2B or 2D) is a direction having a smaller attenuation. In the case where the object is the body of a human and lies on his or her back, the 0° direction or 180° direction (FIG. 2A or 2C) is a direction having a smaller attenuation. Such information is stored in the memory beforehand. It is of course that information indicating directions with smaller attenuation for other parts and in the case of the sideway position of the object is also stored in the memory.

The direction of smaller attenuation may also be determined from the actual data measured by scanning on the object. Two scanning processes are taken. The first scan (preliminary scanning) is started at any position to measure the attenuation. The direction of smaller attenuation is determined from the actual data of the first scan. The second scan is started at the position of smaller attenuation direction to get the image data of the object.

In step 33, it has been determined on the basis of the input protocol information that the part to be measured is a head. In the case of the measurement of the head in a state in which the object normally lies face up or face downward, a measurement mode is set such that an imaging start position is 90° or 270° (step 33). Namely, when a control instruction is issued from the image processing unit 6 to the scanner control unit 8, the scanner control unit 8 waits for the actual measurement start instruction in the state of a measurement mode set through a series of scanner controls with a measurement start position set to the horizontal axis (90° or 270°). On the other hand, in the case of the measurement of the head in a state in which the object normally faces sideways, an imaging start position is set to 0° or 180°.

In step 34, it has been determined on the basis of the input protocol information that the part to be measured is a body. In the case of the measurement of the body in a state in which the object normally lies on its back or on its belly, a measurement mode is set such that an imaging start position is 0° or 180° (step 34). When a control instruction for this measurement mode is issued from the image processing unit 6 to the scanner control unit 8, the scanner control unit 8 waits for the actual measurement start instruction in the state of a measurement mode set through a series of scanner controls with a measurement start position set to the vertical axis (0° or 180°). On the other hand, in the case of the measurement of the belly in a state in which the object normally turns sideways or lies on its side, an imaging start position is set to 90° or 270°.

In step 35, the scanner control unit 8 starts the measurement by recognizing the input of the measurement start instruction by the operator from the control console 7. Since the subsequent operation is the same as that having already been explained in the first part of the explanation concerning the present embodiment, the repeated explanation thereof will be omitted.

Figure 4:
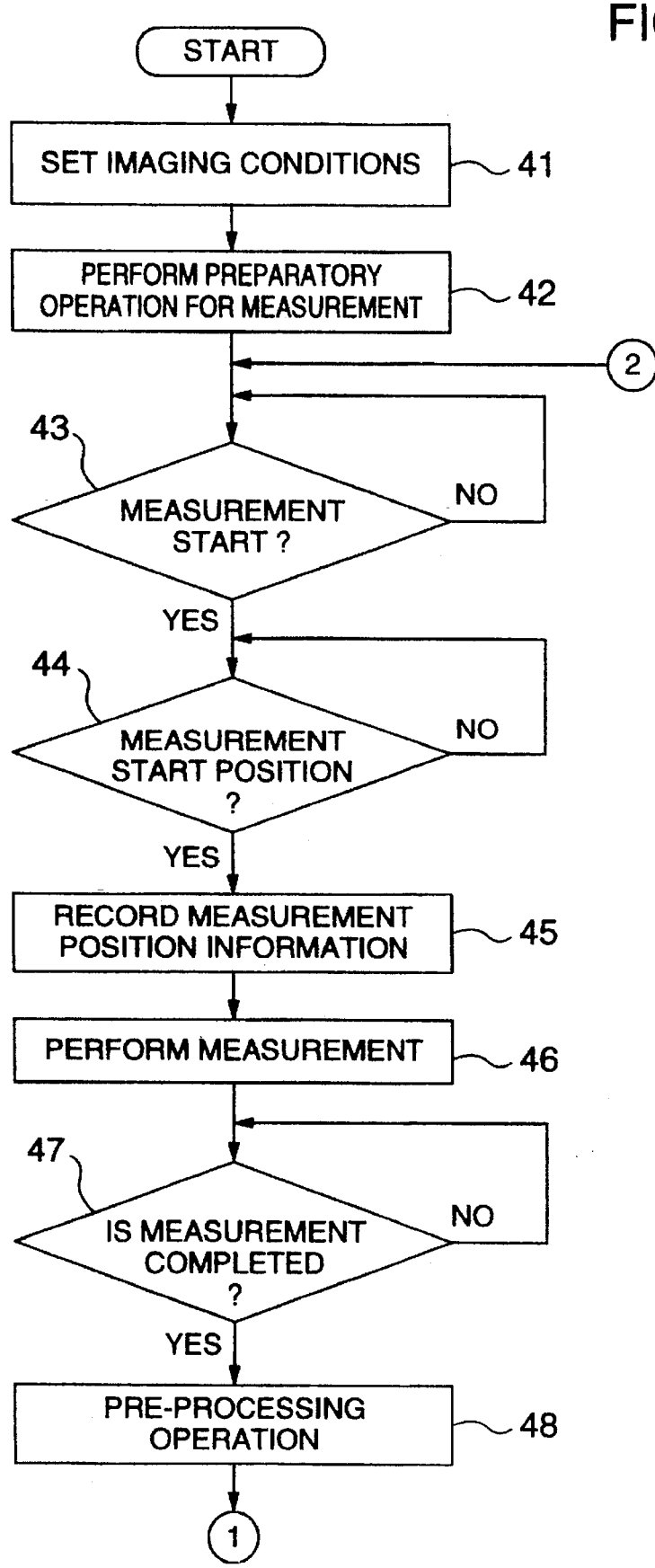
FIGS. 4 and 5 are flow charts for explaining the first and latter halves of an imaging operation in another embodiment of an X-ray medical diagnosis CT apparatus according to the present invention.
Figure 5:
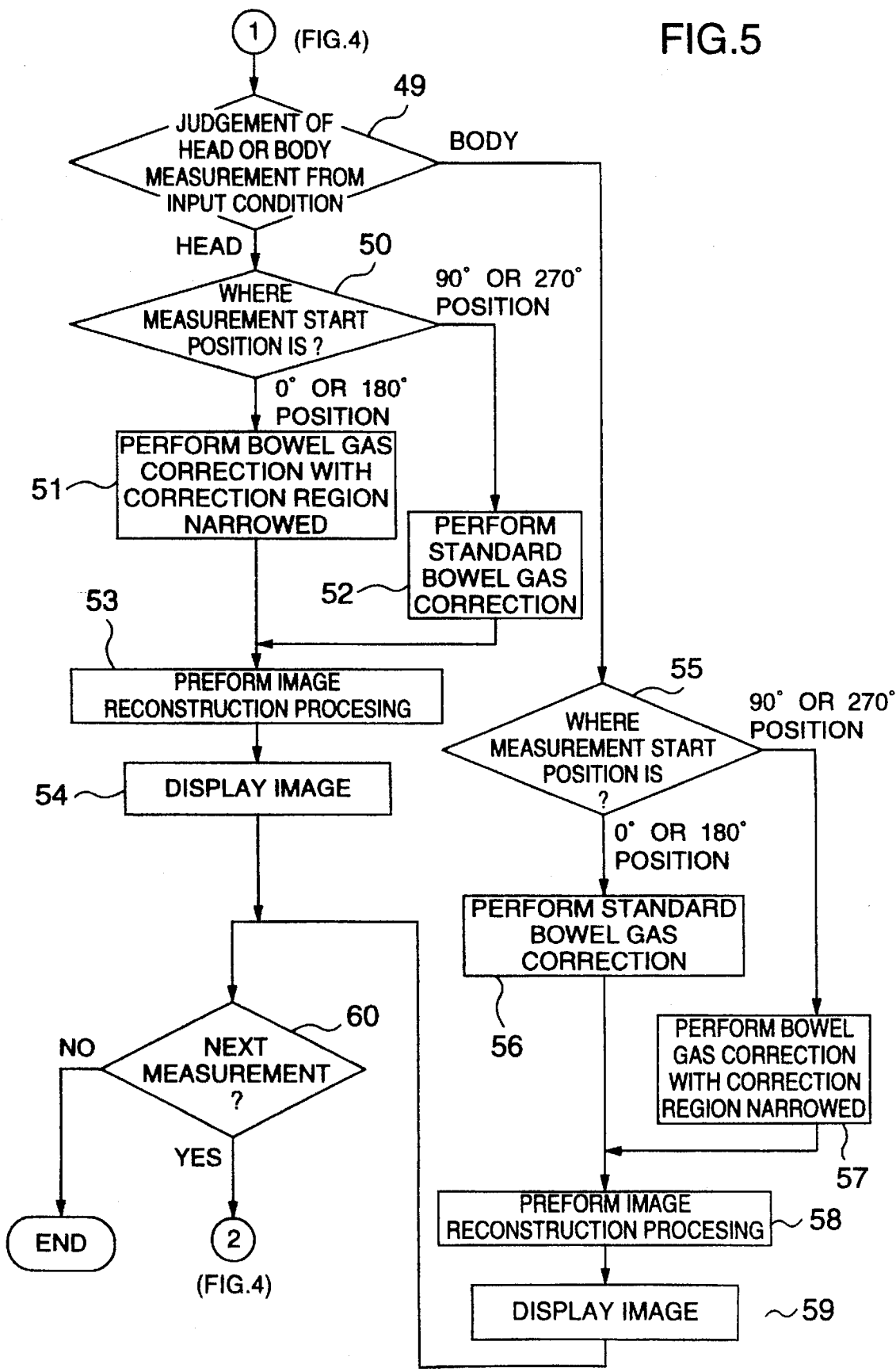
Figure 6:
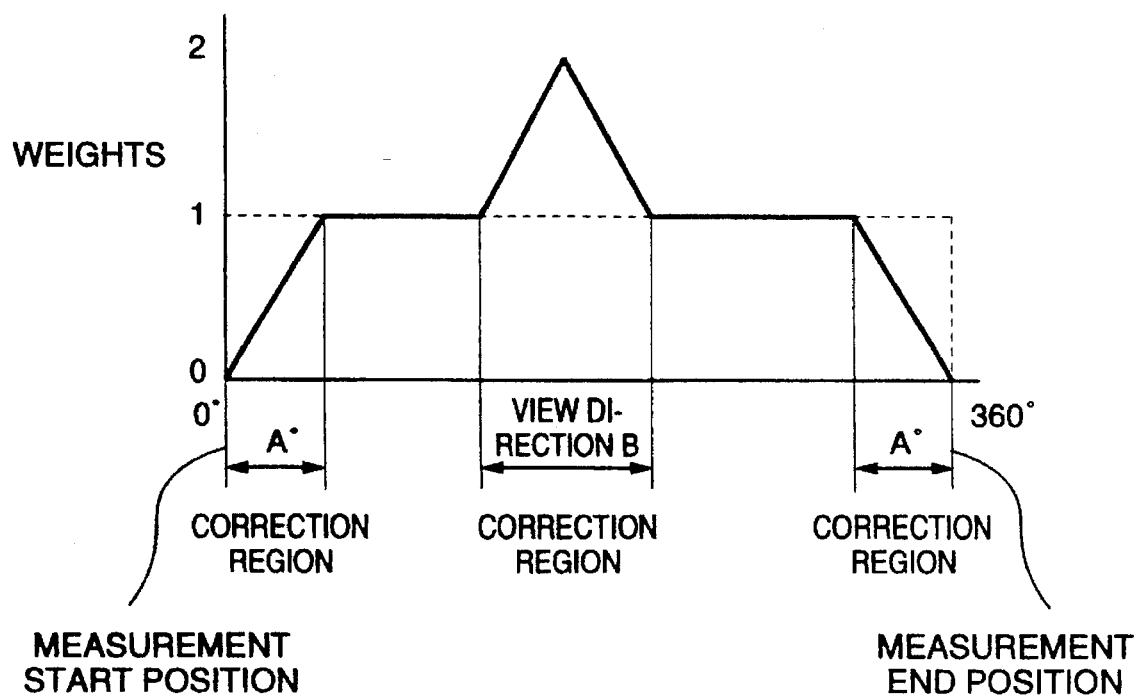
FIG. 6 is a diagram for explaining a bowel gas correction method according to the prior art.
Figure 7A:
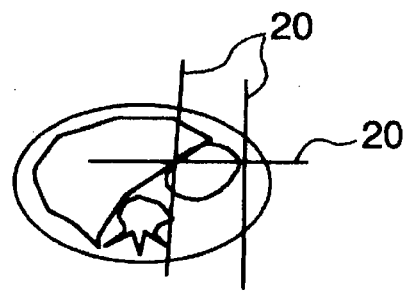
FIGS. 7A, 7B, 7C and 7D are diagrams for explaining the effects and demerits of bowel gas correction.
Figure 7B:
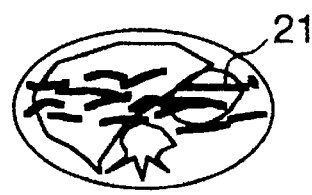
Figure 7C:
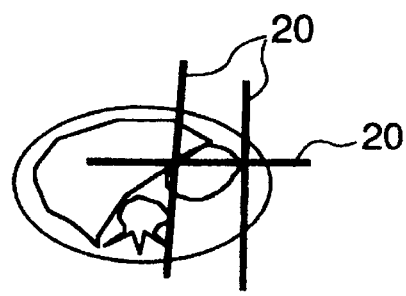
Figure 7D:
Figure 8:
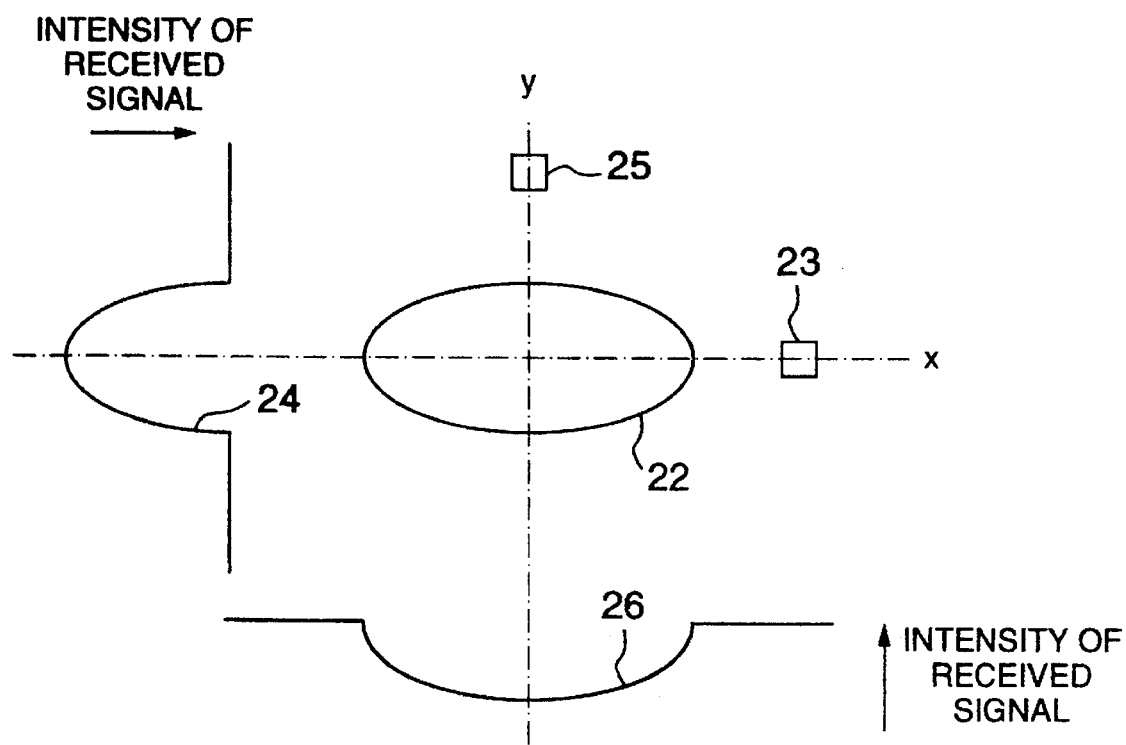
FIG. 8 is a diagram showing a difference in attenuation depending on the direction of irradiation of an object with X-rays.

FIGS. 4 and 5 show the flow of an operation performed in another embodiment of a CT apparatus. In the present embodiment, a relationship between the attenuation of measurement data in axial direction and the measurement start position is judged. In the case where the measurement is started from an axial direction having a large attenuation in an object, a correction processing is performed in such a manner that the correction angle region A (see FIG. 6) to be subjected to a correction data processing for bowel gas correction is made narrower than a normally set width.

In step 41, various settings and measurement conditions necessary for measurement are protocol-inputted by an operator from the control console unit 7. The details of the contents of settings in the protocol input are similar to those in step 31 having already been explained in conjunction with FIG. 3.

In step 42, a preparatory operation for measurement is performed. Namely, the image processing unit 6 reads the protocol input information to sent desired control signals to components, such as a high voltage generator for X-rays, a bed unit and the scanner control unit 8, which form the CT apparatus. After the communication of the control signals between those components, a series of operations are performed so that a measurement start instruction waiting condition is taken at the point of time when the preparations for measurement are completed. In the case where the measurement operation is performed while making a clockwise or right-handed rotation of a scanner and the scanner is of the general type, the measurement start instruction waiting condition means a condition in which the scanner stands by at an angle position on the minus side of the measurement start position of 0° in FIG. 1. In the case where the scanner has a slip ring structure and a continuous rotation has already been started, the measurement start instruction waiting condition means a condition in which there is ready to start the measurement at any time by generating X-rays.

In step 43, a controller (not shown) of the image processing unit 6 continually confirms whether or not an operation such as measurement start button or instruction key input by the operator is made. In the case where a measurement instruction is not issued, step 43 is repeated until the operation such as measurement start button or instruction key input by the operator is confirmed. In the case where the confirmation is obtained, the flow proceeds to a measuring operation which will be explained in the following.

In step 44, the scanner control unit 8 judges whether or not there reaches a measurement start position which the scanner first passes after the turn to a measuring operation condition. The judgement is made by confirming a signal from the position sensors (91 to 94 in FIG. 1). This operation is continued until the measurement start position is confirmed.

In step 45, a measurement start signal is sent to the controller of the image processing unit 6 and other control units so that the measurement is started at the point of time when the first confirmed position sensor signal is received. Also, at this point of time, a signal indicating the present measurement start position is sent to the image processing unit 6 and recorded therein. The correspondence of the measurement start position to the measurement data sent to the image processing unit 6 is possible by, for example, a method in which a table associated with the addresses of storage positions of a memory is prepared or a method in which position information is recorded in the first field of measurement data. In step 46, the generation of X-rays and the taking-in of measurement data are started to perform the actual measurement operation.

In step 47, the controller of the image processing unit 6 judges whether or not a series of measurements are completed. Simultaneously with the completion, the flow goes to step 48. The series of measurements correspond to one of various measurement modes including a mode in which the measurement for only one slice is involved, a mode in which the continuous measurement for plural slices is involved and a mode in which an operation processing is performed after the completion of the whole of a series of measurements. The designation of this measurement mode is inputted by the operator when the imaging conditions are set in step 41. The following explanation will be made assuming a measurement mode in which an operation processing is performed for each one slice measurement, an image is displayed and a wait is thereafter taken for an instruction for start of the next slice measurement.

Step 48 is a processing which is performed in the usual CT apparatus, for example, a pre-processing such as the LOG conversion processing of measurement data or the correction of various sensitivities. In step 49, the judgement of a relationship in quantity of attenuation in the object is made from the conditions inputted in step 41. Since the judging method is similar to that in step 32 shown in FIG. 3, the explanation thereof will be omitted. However, processings in and after step 50 will be explained assuming that the determination of an imaging part of the object based on the conditions set in step 41 results in that the object is in a supine position.

In step 50 taken in the case where the determination of "head" measurement is made, the measurement start position recorded in step 45 is confirmed. As a result, the flow goes to step 51 when the measurement start position is 0° or 180° and to step 52 when the measurement start position is 90° or 270°.

In step 51, the part to be measured is a head in a supine position and the vertical direction (or major axis direction) having a large attenuation coincides with the scanner measurement start position (0° or 180°). Therefore, the correction is performed with the range of the correction region A (see FIG. 6) for bowel gas correction being made narrower than a usual standard width. In step 52, on the other hand, the bowel gas correction is performed in the usual standard width since the vertical direction having the large attenuation in the head or part to be measured does not coincide with the scanner measurement start position (90° or 270°).

In step 53, a usual image reconstruction processing in the CT apparatus is performed. In step 54, a reconstructed cross-sectional image is displayed on the image display device of the control console 7.

In step 55 taken when the determination of "belly" measurement is made, the recorded measurement start position is confirmed. Then, the flow goes to step 56 when the measurement start position is 0° or 180° and to step 57 when the measurement start position is 90° or 270°.

In step 56, the bowel gas correction is performed in the usual standard width since an axial direction having a large attenuation in the belly or part to be measured (or the horizontal direction) does not coincide with the scanner measurement start position (0° or 180°). On the other hand, in step 57, the correction is performed with the range of the correction region A (see FIG. 6) for bowel gas correction made narrower than the usual standard width since the axial direction having the large attenuation in the belly or part to be measured (or the horizontal direction) coincides with the scanner measurement start position (00° or 270°).

Steps 58 and 59 are the same as steps 53 and 54 mentioned above. In step 60, the judgement is made of whether or not the series of measurement operations inputted in step 41 are completed. In the case of the completion, the judgement is made of whether or not there is the next measurement. When the result of judgement is negative, the processing is completed. When the result of judgement is affirmative, the flow returns to step 43 in order to perform the operations in steps 43 to 60.

For the purpose of simplifying the judgement of the attenuation in the axial direction of an object, the foregoing embodiments have been explained in conjunction with the case where the axial directions are two directions which include the vertical axis direction and the horizontal axis direction. However, the axial directions are not limited to the two directions of the vertical and horizontal axes and can include any other directions from the gist of the present invention. In this case, the setting of a measurement start position is possible to a plurality of positions. In the foregoing embodiments, the judgement of the quantity of attenuation in the axial direction has been made referring to measurement conditions inputted by the control console 7. However, another judging method is also possible. For example, in the example shown in FIGS. 4 and 5, the view projection data of measurement data at the measurement start position and a position shifted from the measurement start position by 90° are stored in the memory and can be read therefrom later on. Therefore, the determination of which one of the axial directions has a large attenuation can be made with a higher precision by comparing the average value or total sum of projection data in a central channel (ch) width corresponding to the measurement start position and that corresponding to the 90° shifted position.

In the foregoing embodiments, the bowel gas correction has been made in reference to the measurement data correcting method disclosed by U.S. Pat. No. 5,580,219. However, it is needless to say that a variety of other methods for weighted conversion of data in measurement start/end position region are applicable in the present invention. For example, even in the case where the object of weighting is limited to only the A° region near the measurement start or end position, the motion artifacts can be reduced. In this case, data in a region in A° from the measurement start position 0° is converted into, for example, data weighted in proportion to the positions of 360° data and A° data.

In the embodiment shown in FIGS. 4 and 5, or more especially, in steps 44 and 45, the scanner control unit 8 confirms the arrival of the scanner to a measurement start point which the scanner first passes subsequently to the turn to a measurement operating condition after the operator's measurement start instruction. The confirmation is made on the basis of a signal from the position sensors (91 to 94 in FIG. 1). The measurement is started at the point of time when the first confirmed position sensor signal is received. With such an operation, a plurality of measurement start positions corresponding to the kinds of measurement times can be provided even in a scanner based on a control method in which the measurement is started from a fixed position. Thereby, it becomes possible to maintain the concurrency of the operator's measurement start operation and the actual measurement start irrespective of a difference in length between measurement times associated with various measurement modes and to minimize the variations in delay time. Therefore, it is not necessary that the operator performs the operation while taking the various measurement modes and a time until the start of measurement into consideration.

According to the control method of the disclosed embodiment, a plurality of measurement start positions of a scanner (four positions in the shown embodiment) are provided corresponding to a plurality of measurement time modes of the scanner and the measurement is started from a measurement start position which the scanner first reaches after the lapse of a time from the judgement of a measurement start instruction until the completion of preparations for measurement. More particularly, the present embodiment assumes that a CT apparatus capable of selecting, for example, three kinds of measurement modes of 1 second, 2 seconds and 4 seconds is realized by a scanner which can perform the measurement from four fixed measurement start positions of 0° (360°), 90°, 180° and 270°.

In general, a preparatory time for measurement start is common to all measurement time modes and a difference in measurement time between the modes corresponds to a difference in rotation speed of the scanner. Therefore, with the provision of the plurality of measurement start positions (four positions in the present embodiment) corresponding to the measurement time modes, the region of movement of the scanner in a time from the operator's measurement start designation to the completion of preparations for measurement will extend over, for example, four measurement start positions in the case of the shorter (or 1-second) time mode and two measurement start positions in the case of the longer (or 4-second) time mode. Accordingly, with the construction in which the plurality of measurement start positions are provided corresponding to the measurement time modes and the measurement is started from a measurement start point which the scanner first passes after the turn to a measurement operating condition, it is possible to uniformalize a time from the designation of the start of measurement until the arrival to the next measurement start position after the completion of preparations for measurement. Thereby, even in a scanner which cannot freely perform a measurement start operation or a scanner based on a control method in which the measurement is started from a fixed position, it becomes possible to provide a high-quality cross-sectional image with a high efficiency of measurement even in the case of an imaging which uses a contrast agent or the measurement of an object which is subject to frequent motions.

The setting of the plurality of measurement start positions is similar to that explained in conjunction with FIG. 1. Namely, the position sensors 91 to 94 for reading the measurement start mark of the position information plate 9 are fixed on the scanner base side which is not rotated. When the measurement start mark on the position information plate 9 passes one of the position sensors 91 to 94, a detection signal from the position sensor is delivered to the scanner control unit 8 which makes the whole control of the measurement operation of the scanner. The scanner control unit 8 determines which one of the sensors 91 to 94 delivers the detection signal. Thus, the scanner control unit 8 can control the timing of a measurement start position while confirming the rotation angle of the scanner. In the case where the position information plate 9 is marked beforehand with encoded signals at positions corresponding to four angle positions, the judgement of scanner angle information is possible by reading a position information signal from only a position sensor fixed at one location.

In the above embodiment, the measurement time has been explained in conjunction with the case where the combination of doubly increasing measurement times is taken by way of example. However, the present invention is also applicable to a CT apparatus which may involve many various measurement times. In this case, the concurrency of the operator's measurement start operation and the actual measurement start can be improved by setting an increased number of measurement start positions in an increased number of directions.

As apparent from the foregoing explanation, the present invention makes it possible to suppress, for various objects, the increase of background noises necessarily associated with motion artifact correction while maintaining the effect of motion artifact correction. As a technically excellent effect, therefore, a CT apparatus is offered which can provide a high-quality cross-sectional image necessary for accurate diagnosis of a patient in the capacity of a medical diagnosis apparatus.

According to the present invention, it is possible to maintain the concurrency of the operator's measurement start operation and the actual measurement start irrespective of a difference in length between measurement times in various measurement modes and to minimize the variations in delay time. As a technically excellent effect, a medical diagnosis CT apparatus is offered which has no need to use the apparatus while taking various measurement modes and a time until the start of measurement into consideration, has a high efficiency of measurement and can provide a high-quality cross-sectional image even in the case of an imaging which uses a contrast agent or the measurement of an object which is subject to frequent motions.

What is claimed is:

1. A computed-tomography apparatus for acquiring a cross-sectional image of an object on the basis of projection data of said object obtained by scanning said object with radiation while rotating a scanner around said object, comprising:

image processing means for assigning individual weights to projection data in a predetermined rotation angle range including the vicinity of a scan start rotation position of said scanner and the vicinity of a scan end rotation position thereof and projection data in a rotation angle range opposite to said predetermined rotation angle range, respectively, determining corrected data for the entire circumference of said object by use of the projection data assigned with said weights and projection data assigned with no weight, and generating said cross-sectional image on the basis of said corrected data;

determining means for determining one of rotation positions of said scanner which has a smaller attenuation of radiation; and scanner controlling means for controlling the operation of said scanner so that the scan is started from said rotation position having the smaller attenuation.

2. A computed-tomography apparatus according to claim 1, wherein said determining means includes storage means for holding information indicating a direction of said object which has a smaller attenuation, and when information concerning the orientation of said object relative to said scanner is given, said determining means determines said rotation position having the smaller attenuation on the basis of said information.

3. A computed-tomography apparatus according to claim 1, wherein said determining means determines said rotation position having the smaller attenuation on the basis of projection data obtained when said object is scanned by said scanner.

4. A computed-tomography apparatus according to claim 3, wherein said determining means includes means for determining an average value of projection data obtained through the scan of a predetermined rotation angle range, said determining means determining said rotation position having the smaller attenuation by comparing projection data in a plurality of predetermined different rotation angle ranges.

5. A computed-tomography apparatus according to claim 1, further comprising position detecting means for detecting a scan start rotation position of said scanner, wherein four scan start rotation positions are set on the locus of scan rotation of said scanner at the intervals of 90° rotation angle, said determining means determines one of said four scan start rotation positions having the smallest attenuation, and said scanner controlling means starts the measurement when said position detecting means detects the scan start rotation position having the smallest attenuation.

6. A computed-tomography apparatus for acquiring a cross-sectional image of an object on the basis of projection data of said object obtained by scanning said object with radiation while rotating a scanner around said object, comprising:

image processing means for assigning individual weights to projection data in a predetermined rotation angle range including the vicinity of a scan start rotation position of said scanner and the vicinity of a scan end rotation position thereof and projection data in a rotation angle range opposite to said predetermined rotation angle range, respectively, determining corrected data for the entire circumference of said object by use of the projection data assigned with said weights and projection data assigned with no weight, and generating said cross-sectional image on the basis of said corrected data;

determining means for determining one of rotation positions of said scanner which has a smaller attenuation of radiation;

position detecting means for detecting a scan start rotation position of said scanner; and correction range adjusting means for narrowing said predetermined rotation angle range in the case where the scan start rotation position is not the rotation position having the smaller attenuation.

7. A computed-tomography apparatus according to claim 6, wherein said determining means includes storage means for holding information indicating a direction of said object which has a smaller attenuation, and when information concerning the orientation of said object relative to said scanner is given, said determining means determines said rotation position having the smaller attenuation on the basis of said information.

8. A computed-tomography apparatus according to claim 6, wherein said determining means determines said rotation position having the smaller attenuation on the basis of projection data obtained when said object is scanned by said scanner.

9. A computed-tomography apparatus according to claim 8, wherein said determining means includes means for determining an average value of projection data obtained through the scan of a predetermined rotation angle range, said determining means determining said rotation position having the smaller attenuation by comparing projection data in a plurality of predetermined different rotation angle ranges.

10. A computed-tomography apparatus according to claim 6, wherein four scan start rotation positions are set on the locus of scan rotation of said scanner at the intervals of 90° rotation angle, said determining means determines one of said four scan start rotation positions having the smallest attenuation, and said correction range adjusting means includes means for judging whether or not the actual scan start rotation position detected by said position detecting means is said scan start rotation position having the smallest attenuation.

11. A computed-tomography apparatus for acquiring a cross-sectional image of an object on the basis of projection data of said object obtained by scanning said object with radiation while rotating a scanner around said object, comprising:

image processing means for generating said cross-sectional image on the basis of projection data obtained from the start of scan by said scanner until the end thereof;

a plurality of scan start rotation positions set on the locus of scan rotation of said scanner;

position detecting means for detecting said plurality of scan start rotation positions during the rotation of said scanner; and scanner controlling means for starting the actual scan from the scan start rotation position which said position detecting means first detects after the point of time when a scan start signal is given.

12. A control method in a computed-tomography apparatus for acquiring a cross-sectional image of an object on the basis of projection data of said object obtained by scanning said object with radiation while rotating a scanner around said object, comprising the steps of:

determining one of rotation positions of said scanner which has a smaller attenuation of radiation;

controlling the operation of said scanner so that the scan is started from said rotation position having the smaller attenuation; and assigning individual weights to projection data in a predetermined rotation angle range including the vicinity of a scan start rotation position of said scanner and the vicinity of a scan end rotation position thereof and projection data in a rotation angle range opposite to said predetermined rotation angle range, respectively, determining corrected data for the entire circumference of said object by use of the projection data assigned with said weights and projection data assigned with no weight, and generating said cross-sectional image on the basis of said corrected data.

13. A control method in a computed-tomography apparatus for acquiring a cross-sectional image of an object on the basis of projection data of said object obtained by scanning said object with radiation while rotating a scanner around said object, comprising the steps of:

determining one of rotation positions of said scanner which has a smaller attenuation of radiation;

detecting a scan start rotation position of said scanner;

assigning individual weights to projection data in a predetermined rotation angle range including the vicinity of a scan start rotation position of said scanner and the vicinity of a scan end rotation position thereof and projection data in a rotation angle range opposite to said predetermined rotation angle range, respectively, determining corrected data for the entire circumference of said object by use of the projection data assigned with said weights and projection data assigned with no weight, and generating said cross-sectional image on the basis of said corrected data; and narrowing said predetermined rotation angle range in the case where the detected scan start rotation position is not the rotation position having the smaller attenuation.

14. A control method in a computed-tomography apparatus for acquiring a cross-sectional image of an object on the basis of projection data of said object obtained by scanning said object with radiation while rotating a scanner around said object, comprising the steps of:

setting a plurality of scan start rotation positions on the locus of scan rotation of said scanner;

detecting said plurality of scan start rotation positions during the rotation of said scanner;

starting the actual scan from the scan start rotation position which is first detected after the point of time when a scan start signal is given; and generating said cross-sectional image on the basis of projection data obtained from the start of scan by said scanner until the end thereof.

15. A computed-tomography apparatus for acquiring a cross-sectional image of an object on the basis of projection data of said object obtained by scanning said object with radiation while rotating a scanner around said object, comprising:

determining means for determining one of rotation positions of said scanner which has a smaller attenuation of radiation; and scanner controlling means for controlling the operation of said scanner so that the scan is started from said rotation position having the smaller attenuation.

16. A computed-tomography apparatus according to claim 15, wherein said determining means includes storage means for holding information indicating a direction of said object which has a smaller attenuation, and when information concerning the orientation of said object relative to said scanner is given, said determining means determines said rotation position having the smaller attenuation on the basis of said information.

17. A computed-tomography apparatus according to claim 15, wherein said determining means determines said rotation position having the smaller attenuation on the basis of projection data obtained when said object is scanned by said scanner.

18. A computed-tomography apparatus according to claim 17, wherein said determining means includes means for determining an average value of projection data obtained through the scan of a predetermined rotation angle range, said determining means determining said rotation position having the smaller attenuation by comparing projection data in a plurality of predetermined different rotation angle ranges.

19. A computed-tomography apparatus according to claim 15, further comprising position detecting means for detecting a scan rotation position of said scanner, wherein four scan start rotation positions are set on the locus of scan rotation of said scanner at the intervals of 90° rotation angle, said determining means determines one of said four scan start rotation positions having the smallest attenuation, and said scanner controlling means starts the measurement when said position detecting means detects the scan start rotation position having the smallest attenuation.

20. A computed-tomography apparatus according to claim 15, further comprising position detecting means for detecting a scan rotation position of said scanner.

21. A computed-tomography apparatus according to claim 20, wherein two scan start rotation positions are set on the locus of scan rotation of said scanner at the intervals of approximately 90° rotation angle, said determining means determines one of said two scan start rotation positions having the smaller attenuation, and said scanner controlling means starts the measurement when said position detecting means detects the scan start rotation position having the smaller attenuation.

22. A computed-tomography apparatus for acquiring a cross-sectional image of an object on the basis of projection data of said object obtained by scanning said object with radiation while rotating a scanner around said object, comprising:

image processing means for assigning individual weights to projection data in a predetermined rotation angle range including the vicinity of a scan start rotation position of said scanner and the vicinity of a scan end rotation position thereof and projection data in a rotation angle range opposite to said predetermined rotation angle range, respectively, determining corrected data for the entire circumference of said object by use of the projection data assigned with said weights and projection data assigned with no weight, and generating said cross-sectional image on the basis of said corrected data;

determining means for determining one of rotation positions of said scanner which has a smaller attenuation of radiation;

position detecting means for detecting a scan start rotation position of said scanner; and correction range adjusting means for changing said predetermined rotation angle range in accordance with the scan start rotation position.

23. A computed-tomography apparatus for acquiring a cross-sectional image of an object on the basis of projection data of said object obtained by scanning said object with radiation while rotating a scanner around said object, comprising:

image processing means for generating said cross-sectional image on the basis of projection data obtained from the start of scan by said scanner until the end thereof;

position information provided on a rotating portion of said scanner;

position detecting means for detecting a plurality of scan start rotation positions of said scanner during the rotation of said scanner on the basis of said position information; and scanner controlling means for starting the actual scan from the scan start rotation position which said position detecting means first detects after the point of time when a scan start signal is given.

24. A computed-tomography apparatus according to claim 23, wherein said position detecting means sets a number of the scan start rotation positions in accordance with a length of a scan rotation time of said scanner.

25. A control method in a computed-tomography apparatus for acquiring a cross-sectional image of an object on the basis of projection data of said object obtained by scanning said object with radiation while rotating a scanner around said object, comprising the steps of:

providing position information on a rotating portion of said scanner;

detecting a plurality of scan start rotation positions of said scanner during the rotation of said scanner on the basis of said position information;

starting the actual scan from the scan start rotation position which is first detected after the point of time when a scan start signal is given; and generating said cross-sectional image on the basis of projection data obtained from the start of scan by said scanner until the end thereof.

* * * * *